United States Patent
Arnold et al.

(10) Patent No.: US 9,364,487 B2
(45) Date of Patent: Jun. 14, 2016

(54) DERMAL DELIVERY COMPOSITIONS AND METHODS

(71) Applicants: Charles G. Arnold, Kinnelon, NJ (US); Agis Kydonieus, Kendall Park, NJ (US); Thomas M. Rossi, Stockton, NJ (US); Alfred F. Altomari, Lawrenceville, NJ (US)

(72) Inventors: Charles G. Arnold, Kinnelon, NJ (US); Agis Kydonieus, Kendall Park, NJ (US); Thomas M. Rossi, Stockton, NJ (US); Alfred F. Altomari, Lawrenceville, NJ (US)

(73) Assignee: Agile Therapeutics, Inc., Princeton, NJ (US)

( * ) Notice: Subject to any disclaimer, the term of this patent is extended or adjusted under 35 U.S.C. 154(b) by 0 days.

(21) Appl. No.: 13/667,632

(22) Filed: Nov. 2, 2012

(65) Prior Publication Data
US 2013/0116222 A1 May 9, 2013

Related U.S. Application Data

(60) Provisional application No. 61/555,546, filed on Nov. 4, 2011, provisional application No. 61/645,778, filed on May 11, 2012.

(51) Int. Cl.
| | | |
|---|---|---|
| *A61K 31/567* | (2006.01) | |
| *A61K 31/57* | (2006.01) | |
| *A61K 47/20* | (2006.01) | |
| *A61K 9/70* | (2006.01) | |
| *A61K 47/32* | (2006.01) | |

(52) U.S. Cl.
CPC .............. *A61K 31/567* (2013.01); *A61K 9/7061* (2013.01); *A61K 31/57* (2013.01); *A61K 47/20* (2013.01); *A61K 47/32* (2013.01)

(58) Field of Classification Search
None
See application file for complete search history.

(56) References Cited

U.S. PATENT DOCUMENTS

| | | | |
|---|---|---|---|
| 7,045,145 B1 | 5/2006 | Chien | |
| 7,384,650 B2* | 6/2008 | Chien | 424/448 |
| 2006/0121102 A1* | 6/2006 | Chiang | 424/449 |
| 2006/0275360 A1* | 12/2006 | Ahmed et al. | 424/451 |
| 2008/0175905 A1* | 7/2008 | Liu et al. | 424/464 |
| 2010/0178323 A1 | 7/2010 | Kydonieus et al. | |
| 2010/0255072 A1 | 10/2010 | Kydonieus et al. | |
| 2010/0292660 A1 | 11/2010 | Kydonieus et al. | |

FOREIGN PATENT DOCUMENTS

| | | |
|---|---|---|
| WO | 95/18603 | 7/1995 |
| WO | 99/15156 | 4/1999 |
| WO | 2006/036899 | 4/2006 |
| WO | 2007/022061 | 2/2007 |

OTHER PUBLICATIONS

Corresponding International Search Report and Written Opinion in PCT/US2012/63314, mailed Mar. 8, 2013.
USPTO Inter Partes Review IPR2014-00549 Exhibit-1010v2 (corrected Ex. 1010, Kydonieus Declaration).
USPTO Inter Partes Review IPR2014-00549 Exhibit-1026 (Trial Transcript Day 1, pp. 1-2 and 117-299).
USPTO Inter Partes Review IPR2014-00549 Exhibit-1030 (Kydonieus Deposition Transcript).
USPTO Inter Partes Review IPR2014-00549 Exhibit-1031 (Kydonieus Reply Declaration, Corrected, Redacted).
USPTO Inter Partes Review IPR2014-00549 Exhibit-1049 (Kydonieus Second Deposition Transcript Redacted).

* cited by examiner

*Primary Examiner* — Jennifer Berrios
(74) *Attorney, Agent, or Firm* — Potter Anderson and Corroon LLP

(57) ABSTRACT

A composition for transdermal delivery of a progestin for progestin hormone therapy is disclosed. Also disclosed is a transdermal delivery device comprising the composition. For progestin-only hormone therapy, the composition contains an anti-oxidant and does not contain an estrogen. For therapy involving a progestin and an estrogen, the composition contains the progestin, the estrogen and an additional anti-oxidant. Methods of improving the stability of progestin-containing compositions comprising oxidative agents are also disclosed. The methods comprise including one or more anti-oxidants in the compositions.

14 Claims, No Drawings

DERMAL DELIVERY COMPOSITIONS AND METHODS

FIELD OF THE INVENTION

This invention is in the field of transdermal delivery of steroid hormones.

BACKGROUND OF THE INVENTION

Various adhesive matrix compositions have been developed for transdermal delivery of steroid hormones. For example, U.S. Pat. No. 7,384,650 describes a transdermal hormone delivery system that utilizes an adhesive composition comprising a pressure sensitive adhesive (PSA), a humectant, a skin permeation enhancer, an estrogen and a progestin.

U.S. Patent Publications 2010/0292660 and 2010/0255072 describe transdermal delivery systems that can be used, among other ways, in conjunction with the PSA matrix described in U.S. Pat. No. 7,384,650.

The above-cited patent and patent applications are incorporated by reference as though fully set forth herein.

SUMMARY OF THE INVENTION

This invention relates to a polymeric matrix useful in a transdermal delivery system for transdermal delivery of a progestin, in the absence of an estrogen.

One aspect of the invention features composition for transdermal delivery of a progestin that comprises: (a) a carrier, (b) a progestin, (c) a skin permeation enhancer and (d) an anti-oxidant, wherein the composition comprises a component that contributes to degradation of the progestin, wherein the component is one or more of an organic solvent, polyvinyl pyrrolidone (PVP), or a PVP copolymer. In one embodiment, the carrier is a polymeric pressure sensitive adhesive. In one embodiment, the component that contributes to degradation of the progestin is one or more of PVP, polyvinyl pyrrolidone/vinyl acetate (PVP/VA), or dimethyl sulfoxide (DMSO) and the anti-oxidant is not an estrogen or is additional to an estrogen.

The progestin can be desogestrel, dihydroprogesterone, drospirenone, ethynodiol acetate, ethynodiol diacetate, etogestrel, gestodene, gestogen, 17-hydrogesterone, hydroxyprogesterone caproate, 3-keto-desogestrel, levonorgestrel, medroxyprogesterone acetate, medroxyprogesterone diacetate, megestrol, megestrol acetate, normegesterol, norelgestromin, norethindrone (i.e., norethisterone), norethindrone acetate, norethynodrel, norgestimate, norgestrel, 19-nortestosterone, progesterone, nestorone, methoxyprogesterone, or dl-norgestrel, or any combination of two or more of said progestins. In certain embodiments, the progestin is levonorgestrel or norethindrone acetate.

The anti-oxidant is selected from Vitamins A, C, D, and E, carotenoids, flavanoids, isoflavanoids, beta-carotene, butylated hydroxytoluene ("BHT"), butylated hydroxyanisole (BHA), glutathione, lycopene, gallic acid and esters thereof, salicylic acid and esters thereof, sulfites, alcohols, amines, amides, sulfoxides, surfactants, or any combination thereof. In certain embodiments, the anti-oxidant is sodium bisulfite, sodium sulfite, isopropyl gallate, Vitamin C and E, Irganox 1010, Irgafos 168 or BHT or any combination of two or more of those anti-oxidants. In certain embodiments, the anti-oxidant comprises one or more phenolic anti-oxidants. In particular, the anti-oxidant is BHT, pentaerythritol tetrakis(3-(3,5-di-tert-butyl-4-hydroxyphenyl)propionate), or tris(2,4-di-tert-butylphenyl)phosphite.

In certain embodiments, the polymeric carrier is a pressure sensitive adhesive (PSA) selected from a polyacrylate adhesive, a polyisobutylene adhesive, or a silicone adhesive. The PSA may be polymerized by free radical polymerization. For instance, the PSA can be a polyacrylate adhesive. The PSA may comprise a 2-ethylhexyl acrylate co-monomer. The polyacrylate adhesive can further comprise about 50 to 60% w/w vinyl acetate co-monomer.

In certain embodiments, the skin permeation enhancer comprises one or more of: alcohols; alkanones; amides and other nitrogenous compounds; 1-substituted azacycloheptan-2-ones; bile salts; cholesterol; cyclodextrins and substituted cyclodextrins; ethers; saturated and unsaturated fatty acids; saturated and unsaturated fatty acid esters; saturated and unsaturated fatty alcohol esters; glycerides and monoglycerides; organic acids; methyl nicotinate; pentadecalactone; polyols and esters thereof; phospholipids; sulfoxides; surfactants; terpenes; and combinations thereof. In one embodiment, the skin permeation enhancer comprises an organic solvent. In some instances, the organic solvent is DMSO. In certain embodiments, the skin permeation enhancer comprises one or more of: DMSO, a fatty ($C_8$-$C_{20}$) alcohol ester of a hydroxy acid, a lower ($C_1$-$C_4$) alkyl ester of a hydroxy acid, and a $C_6$-$C_{18}$ fatty acid. In a particular embodiment, the skin permeation enhancer comprises one or more of: DMSO, lauryl lactate, ethyl lactate, and capric acid.

The above-described composition can also include a humectant. In certain embodiments, the humectant is PVP or a PVP co-polymer, such as PVP/VA.

In various embodiments of the above-described composition, the progestin is present in a concentration based on weight of the composition of 0.1% to 3.0% or 0.2% to 2.0% or 0.5% to 1.5%. The skin permeation enhancer can present in a concentration based on weight of the composition of 1% to 50% or 2% to 40%.

In certain embodiments, the anti-oxidant in the composition includes BHT. The BHT can be present in a concentration based on weight of the hormone of 10% to 500%, 20% to 200%, or 50% to 150%.

In certain embodiments, the composition may be one that does not comprise an estrogen.

In certain embodiments, the anti-oxidant in the composition is pentaerythritol tetrakis (3-(3,5-di-tert-butyl-4-hydroxyphenyl) propionate) or tris (2,4-di-tert-butylphenyl)phosphite.

Another aspect of the invention features a transdermal drug delivery device that comprises: (a) a transdermal composition as summarized above, which comprises a PSA and has a skin contacting surface and a non-skin contacting surface; (b) a release liner adjacent the skin contacting surface of the transdermal composition; and (c) a backing layer adjacent the non-skin contacting surface.

Another aspect of the invention features a method of improving the stability of a progestin-only transdermal delivery composition that includes an oxidizing agent. The method comprises adding an anti-oxidant other than an estrogen to the composition. In certain embodiments, the oxidizing agent is one or more of an organic solvent, PVP, or a PVP copolymer. In certain embodiments, the composition comprises a PSA. The progestin can be desogestrel, dihydroprogesterone, drospirenone, ethynodiol acetate, ethynodiol diacetate, etogestrel, gestodene, gestogen, 17-hydrogesterone, hydroxyprogesterone caproate, 3-keto-desogestrel, levonorgestrel, medroxyprogesterone acetate, medroxyprogesterone diacetate, megestrol, megestrol acetate, normegesterol, norelgestromin, norethindrone (norethisterone), norethindrone acetate, norethynodrel, norgestimate, norgestrel, 19-nortestosterone, progesterone, nestorone, methoxyprogesterone, and d1-norgestrel or any combination of two or more of said progestins. In particular, the progestin is levonorgestrel or norethindrone acetate.

In certain embodiments of the method, the anti-oxidant is selected from Vitamins A, C, D, and E, carotenoids, flavanoids, isoflavanoids, beta-carotene, butylated hydroxytoluene ("BHT"), butylated hydroxyanisole (BHA), glutathione, lycopene, gallic acid and esters thereof, salicylic acid and esters thereof, sulfites, alcohols, amines, amides, sulfoxides, phenolics or surfactants, or any combination of two or more of said anti-oxidants. In particular, the anti-oxidant is sodium bisulfite, sodium sulfite, isopropyl gallate, Vitamin C and E, Irganox 1010, Irgafos 168 or BHT or any combination of two or more of said anti-oxidants.

In certain embodiments of the method, the polymeric carrier is a PSA selected from a polyacrylate adhesive, a polyisobutylene adhesive, or a silicone adhesive. The PSA may be polymerized by free radical polymerization. For instance, the PSA may be a polyacrylate adhesive. The PSA can comprise a 2-ethylhexyl acrylate monomer. The polyacrylate adhesive can further comprises about 3 to 60% w/w vinyl acetate monomer.

In various embodiments of the method, the skin permeation enhancer in the composition comprises one or more of: alcohols; alkanones; amides and other nitrogenous compounds; 1-substituted azacycloheptan-2-ones; bile salts; cholesterol; cyclodextrins and substituted cyclodextrins; ethers; saturated and unsaturated fatty acids; saturated and unsaturated fatty acid esters; saturated and unsaturated fatty alcohol esters; glycerides and monoglycerides; organic acids; methyl nicotinate; pentadecalactone; polyols and esters thereof; phospholipids; sulfoxides; surfactants; terpenes; and combinations thereof. In certain embodiments, the enhancer comprises an organic solvent. In particular, the organic solvent is DMSO. In certain embodiments, the enhancer comprises one or more of: DMSO, a fatty ($C_8$-$C_{20}$) alcohol ester of a hydroxy acid, a lower ($C_1$-$C_4$) alkyl ester of a hydroxy acid, and a $C_6$-$C_{18}$ fatty acid. In particular, the enhancer comprises DMSO, lauryl lactate, ethyl lactate, and capric acid.

In certain embodiments of the method, the composition further comprises a humectant. The humectant may be PVP or a PVP co-polymer, such as PVP/VA.

In various embodiments of the method, the progestin is present in the composition in a concentration based on weight of the composition of 0.1% to 3.0% or 0.2% to 2.0% or 0.5% to 1.5%. The skin permeation enhancer is present in a concentration based on weight of the composition of 1% to 50% or 2% to 40%.

In various embodiments of the method, the anti-oxidant in the composition is BHT. The BHT may present in a concentration based on weight of the hormone of 10% to 500%, 20% to 200%, or 50% to 150%.

In various embodiments of the method, the anti-oxidant in the composition is pentaerythritol tetrakis (3-(3,5-di-tert-butyl-4-hydroxyphenyl)propionate) or tris (2,4-di-tert-butylphenyl)phosphite.

These and other embodiments, which are more fully described below, are meant to be illustrative and not limiting of the invention.

DETAILED DESCRIPTION OF THE INVENTION

The present invention is useful in delivering a progestin hormone to a patient that can benefit from progestin-only hormone supplementation, i.e., delivery of a progestin with or without concomitant delivery of an estrogen. In an aspect of the present invention, the progestin, in particular, levonorgestrel, is stabilized, i.e., protected from degradation, by incorporation of an anti-oxidant. While ethinyl estradiol itself has anti-oxidizing activity, it is contemplated in accordance with this invention that if an estrogen is present, then a further anti-oxidant that is not an active pharmaceutical ingredient, e.g., that is not ethinyl estradiol or other hormone, is included in the transdermal composition.

As discussed further hereinbelow, certain components of a transdermal composition, such as the transdermal compositions described in U.S. Pat. No. 7,384,650 and hereinbelow, have been found to contribute to degradation of levonorgestrel. Such components include the polyacrylate pressure sensitive adhesive ("PSA"), the PVP humectant (e.g., PVP/VA), and the dimethyl sulfoxide skin permeation enhancer. Incorporation of an excipient that functions as an anti-oxidant can protect the progestin from degradation, i.e., it can slow degradation of the progestin, and thereby increase the shelf life of the composition.

Progestin-containing Transdermal Composition: The composition for transdermal delivery, i.e., systemic delivery through the skin, comprises a progestin, an anti-oxidant, a skin permeation enhancer and a carrier. The composition does not necessarily comprise an estrogen, If it does not, it may be referred to as a "progestin-only transdermal composition". The composition optionally also comprises excipients such as gelling agents, plasticizers, humectants, buffers, and the like. The composition can be formulated and applied to the skin, for instance, as a gel, an ointment, or a spray, or it can be contained within a transdermal delivery device, such as a patch, in which the composition is contained, for example, within a reservoir by a semi-permeable membrane or as a soft polymeric matrix that is in direct contact with the skin, i.e., that is firm enough that a reservoir membrane is not required.

In an illustrative embodiment of the invention, the composition is a polymeric matrix comprising a polymer such as a pressure-sensitive adhesive (PSA) as a carrier, the progestin, the anti-oxidant and the skin permeation enhancer. The polymer can be a pressure sensitive adhesive ("PSA") that forms a biologically acceptable adhesive polymer matrix capable of forming adhesive active-containing thin films or coatings through which the progestin can pass into the skin. Suitable polymers are biologically and pharmaceutically compatible, nonallergenic, insoluble in and compatible with body fluids or tissues with which the device is contacted. The use of water soluble polymers is generally less preferred since dissolution or erosion of the matrix would affect the release rate of the progestin as well as the capability of the dosage unit to remain in place on the skin. So, in certain embodiments, the polymer is non-water soluble.

Suitable progestin transdermal compositions are disclosed, e.g., in U.S. Pat. Nos. 7,045,145 7,384,650, US 20100255072, US 2010292660, and US 20100178323, all of which are incorporated herein by reference as though fully set forth.

Polymers used to form a polymer matrix in the progestin-containing layer can have glass transition temperatures below room temperature such that they are soft and pliable at room temperature. The polymers are preferably non-crystalline but may have some crystallinity if necessary for the development of other desired properties. Cross-linkable monomeric units or sites can be incorporated into such polymers. For example, cross-linking monomers that can be incorporated into polyacrylate polymers include polymethacrylic esters of polyols such as butylene diacrylate and dimethacrylate, trimethylol propane trimethacrylate and the like. Other monomers that provide such sites include allyl acrylate, allyl methacrylate, diallyl maleate and the like.

PSAs that can be used to form the adhesive composition are typically polyacrylate, polyisobutylene, or silicone adhesives. A useful adhesive polymer formulation comprises a polyacrylate adhesive polymer of the general formula (I):

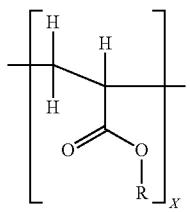

wherein X represents the number of repeating units sufficient to provide the desired properties in the adhesive polymer and R is H or a lower ($C_1$-$C_{10}$) alkyl, such as ethyl, butyl, 2-ethylhexyl, octyl, decyl and the like. The adhesive polymer matrix can comprise, for instance, a polyacrylate adhesive copolymer having a 2-ethylhexyl acrylate monomer and approximately 50-60% w/w of vinyl acetate as a co-monomer. An example of a suitable polyacrylate adhesive copolymer for use in the present invention includes, but is not limited to, that sold under the tradename of Duro Tak® 87-4098 by Henkel Corporation, Bridgewater, N.J., which comprises vinyl acetate co-monomer.

Progestins: Progestins useful in the practice of the present invention include desogestrel, dihydroprogesterone, drospirenone, ethynodiol acetate, ethynodiol diacetate, etogestrel, gestodene, gestogen, 17-hydrogesterone, hydroxyprogesterone caproate, 3-keto-desogestrel, levonorgestrel, medroxyprogesterone acetate, medroxyprogesterone diacetate, megestrol, megestrol acetate, normegesterol, norelgestromin, norethindrone (i.e., norethisterone), norethindrone acetate, norethynodrel, norgestimate, norgestrel, 19-nortestosterone, progesterone, nestorone, methoxyprogesterone, and dl-norgestrel or any combination of two or more of said progestins. Of particular interest are levonorgestrel and norethindrone and norethindrone salts, e.g., norethindrone acetate. Levonorgestrel is a potent progestin on a weight-dose basis and may be selected for that or other reasons. The progestin is typically present in a concentration based on weight of the transdermal composition (i.e., wt %) of 0.1 to 3% or 0.2 to 2.0% or 0.5-1.5%.

Estrogens: Estrogens useful in the practice of the present invention include, without limitation, ethinyl estradiol, 17-beta-estradiol, estradiol-3,17-diacetate; estradiol-3-acetate; estradiol 17-acetate; estradiol-3,17-divalerate; estradiol-3-valerate; estradiol-17-valerate; 3-mono-, 17-mono- and 3,17-dipivilate estradiol esters; 3-mono-, 17-mono- and 3,17-dipropionate estradiol esters; 3-mono-, 17-mono- and 3,17-dicyclo pentyl-propionate estradiol esters, and estrone. Of particular interest is ethinyl estradiol. The estrogen is typically present in a concentration based on weight of the transdermal composition (i.e., wt %) of 0.1 to 3% or 0.2 to 2.0% or 0.5 to 1.5%, e.g., 0.5 to 1%.

Skin Permeation Enhancers: A number of skin permeation enhancers have been used to improve passage of progestins through the skin and into the blood stream. These include, e.g., alcohols; alkanones; amides and other nitrogenous compounds; 1-substituted azacycloheptan-2-ones; bile salts; cholesterol; cyclodextrins and substituted cyclodextrins; ethers; saturated and unsaturated fatty acids; saturated and unsaturated fatty acid esters; saturated and unsaturated fatty alcohol esters; glycerides and monoglycerides; organic acids; methyl nicotinate; pentadecalactone; polyols and esters thereof; phospholipids; sulfoxides; surfactants; terpenes; and combinations thereof.

As specific examples, the following can be mentioned: decanol, dodecanol, 2-hexyl decanol, 2-octyl dodecanol, oleyl alcohol, undecylenic acid, lauric acid, myristic acid and oleic acid, fatty alcohol ethoxylates, esters of fatty acids with methanol, ethanol or isopropanol, methyl laurate, ethyl oleate, isopropyl myristate and isopropyl palmitate, esters of fatty alcohols with acetic acid or lactic acid, lauryl lactate, oleyl acetate, 1,2-propylene glycol, glycerol, 1,3-butanediol, dipropylene glycol and polyethylene glycols.

Of particular interest are volatile organic solvents, including, but not limited to, dimethyl sulfoxide (DMSO), $C_1$-$C_8$ branched or unbranched alcohols, such as ethanol, propanol, isopropanol, butanol, isobutanol, and the like, as well as azone (laurocapram: 1-dodecylhexahydro-2H-azepin-2-one) and methylsulfonylmethane. Also of particular interest are fatty acids and esters thereof.

For example, a skin permeation enhancer useful in the present invention can be a mixture of (1) a pharmaceutically acceptable organic solvent, such as dimethyl sulfoxide (DMSO), (2) a fatty ($C_8$-$C_{20}$) alcohol ester of a hydroxy acid, such as lauryl lactate, (3) a lower ($C_1$-$C_4$) alkyl ester of a hydroxy acid, e.g., ethyl lactate, and (4) a $C_6$-$C_{18}$ fatty acid, such as capric acid. In specific embodiments, the fatty alcohol ester of lactic acid is lauryl lactate and the lower alkyl ester of lactic acid is ethyl lactate. A medium- to long-chain fatty acid in the skin permeation enhancer formulation can be employed among the skin permeation enhancers. Capric acid is preferred for use but other $C_6$-$C_{18}$ saturated or unsaturated fatty acids may be used, including but not limited to caproic acid, caprylic acid, lauric acid and myristic acid, to name a few.

In a particular embodiment, the pharmaceutically acceptable organic solvent is DMSO. Other organic solvents suitable for use in the present invention include, but are not limited to, $C_1$-$C_8$ branched or unbranched alcohols, such as ethanol, propanol, isopropanol, butanol, isobutanol, and the like, as well as azone (laurocapram: 1-dodecylhexahydro-2H-azepin-2-one) and methylsulfonylmethane, to name a few.

The fatty alcohol ester of a hydroxy acid can be a fatty alcohol ester of lactic acid, such as lauryl lactate. However, other hydroxy acids and fatty alcohols may be utilized. Alternative hydroxy acids include, but are not limited to, alpha-hydroxy acids such as glycolic acid, tartaric acid, citric acid, malic acid and mandelic acid, as well as the beta-hydroxy acid, salicylic acid. Alternative fatty alcohols include any $C_8$-$C_{20}$ saturated or unsaturated fatty alcohols, such as myristyl, palmityl or oleyl alcohols, to name a few.

The lower alkyl ester of hydroxy acid can also utilize lactic acid, and can be, e.g., ethyl lactate. However, other hydroxy acids, such as glycolic acid, tartaric acid, citric acid, malic acid, mandelic acid and salicylic acid, may also be utilized. In addition isopropylmyristic acid (IPM) may be used as a substitute for the lower alkyl ester of hydroxy acid.

The aforementioned combination of skin permeation enhancers may be used to enhance transdermal delivery of steroid hormones from any type of transdermal delivery composition, as discussed above. An adhesive polymer matrix-type system as described in detail herein and in U.S. Pat. Nos. 7,045,145, 7,384,650, US 20100255072, US 2010292660, and US 20100178323 are illustrative; however, the enhancer combination may also be utilized in non-adhesive polymers, as well as in multi-layer or reservoir-type transdermal delivery systems, gels, ointments, sprays, and lotions, to name a few.

The skin permeation enhancer is typically present in a concentration of at least 1% or at least 2% by weight of the composition. It may be present in a concentration of up to 50% or up to 40% by weight of the composition. In certain embodiments, the skin permeation enhancer is present in a concentration based on weight of the composition (i.e., wt %) of 1 to 50% or 10 to 40% or 20 to 30% of the composition.

Optional Additional Excipients: A number of excipients are employed in transdermal delivery compositions for various purposes. Of particular interest are polymers that function as humectants and/or as plasticizers. Incorporation of a humectant in the formulation allows the dosage unit to absorb moisture from the surface of skin, which in turn helps to reduce skin irritation and to prevent the adhesive polymer matrix of the delivery system from failing to adhere for a sufficient duration. The plasticizer/humectant may be a conventional plasticizer used in the pharmaceutical industry, for example, polyvinyl pyrrolidone (PVP). In particular, PVP/vinyl acetate (PVP/VA) co-polymers, such as those having a molecular weight of from about 50,000, are suitable for use in the present invention. The PVP/VA acts as both a plasticizer, acting to control the rigidity of the polymer matrix, as well as a humectant, acting to regulate moisture content of the matrix. The PVP/VA can be, for example, Plasdone® S-630 Copovidone (International Specialty Products, Inc. (ISP), Wayne, N.J.), which is a 60:40 PVP:VA co-polymer that has a molecular weight of 24,000 to 30,000 and a glass transition temperature of 106° C. The amount of humectant/plasticizer is directly related to the duration of adhesion of the overlay.

Anti-oxidants: Anti-oxidants function to prevent or inhibit oxidation of other molecules by themselves becoming oxidized. In a polymeric matrix comprising both a progestin and an estrogen such as ethinyl estradiol, the ethinyl estradiol functions as an anti-oxidant and thereby helps to reduce oxidative degradation of the progestin. Employment of an additional anti-oxidant further reduces oxidative degradation. In a progestin-only composition, employment of an anti-oxidant can be even more important.

For example, certain polymers, in particular, polymers formed by free radical polymerization, have been found to act as oxidizing agents in a polymeric matrix comprising a progestin, whereby the stability of the progestin is compromised. For example, it has been discovered in accordance with the present invention that polyacrylate adhesives cause oxidation of a progestin, e.g., levonorgestrel.

It has also been discovered in accordance with the present invention that PVP, which is commonly used in transdermal polymeric compositions, also contributes to oxidation of a progestin. Therefore, in transdermal compositions comprising PVP, or PVP/VA, and a progestin, addition of an anti-oxidant improves the stability of the progestin.

It has also been discovered in accordance with the present invention that certain permeation enhancers, e.g., DMSO, can also cause oxidation of a progestin, e.g., levonorgestrel.

Thus, one aspect of the invention features a polymeric matrix comprising the progestin, the anti-oxidant, the skin permeation enhancer and a pressure sensitive adhesive ("PSA"), wherein the PSA is a polyacrylate adhesive, e.g., a polyacrylate/vinyl acetate copolymer such as Duro Tak® 87-4098, and/or wherein the polymeric matrix comprises PVP or PVP/VA, and/or wherein the permeation enhancer comprises DMSO.

A number of compounds can act as anti-oxidants in the transdermal composition of the present invention. Among compounds known to act as anti-oxidants are: Vitamins A, C, D, and E, carotenoids, flavanoids, isoflavanoids, beta-carotene, butylated hydroxytoluene ("BHT"), butylated hydroxyanisole (BHA), glutathione, lycopene, gallic acid and esters thereof, salicylic acid and esters thereof, sulfites, alcohols, amines, amides, sulfoxides, surfactants, etc. Of particular interest are phenolic anti-oxidants, e.g., BHT, pentaerythritol tetrakis(3-(3,5-di-tert-butyl-4-hydroxyphenyl) propionate), e.g., Irganox 1010, and tris(2,4-di-tert-butylphenyl)phosphite, e.g., Irgafos 168, as well as sodium bisulfite, sodium sulfite, isopropyl gallate, Vitamin C and Vitamin E.

Phenolic anti-oxidants, like BHT, which are sometimes referred to as primary anti-oxidants, are particularly suitable. Larger phenolic anti-oxidants, e.g., molecular weight greater than 500 (e.g., tris(2,4-di-tert-butylphenyl) phosphite) or greater than 1000 (e.g., pentaerythritol tetrakis(3-(3,5-di-tert-butyl-4-hydroxyphenyl)propionate) may be utilized to advantage.

The pH of the transdermal composition can be maintained at about pH 6 to about pH 8, e.g., at about pH 6.0, 6.1, 6.2, 6.3, 6.4, 6.5, 6.6, 6.7, 6.8, 6.9, 7.0, 7.1, 7.2., 7.3, 7.4, 7.5, 7.6, 7.7, 7.8, 7.9 or 8.0. In one embodiment, the composition is maintained at about pH 6.5 to pH7.5. In another embodiment, the composition is maintained at about pH 7. Anti-oxidants that would increase pH, e.g., sodium metabisulfite, are preferably avoided. BHT can be present, e.g., in a concentration based on the weight of the hormone of at least 10 wt % or at least 20 wt % or at least 30 wt % of the hormone. BHT can be present, e.g., in a concentration of up to 150 wt % or 200 wt % or 500 wt % of the hormone. In certain embodiments, BHT is present in a concentration based on weight of the hormone of 10 to 500%, 20 to 200%, or 50 to 150% of the hormone. Suitable concentrations of other anti-oxidants are readily ascertainable. For example, suitable concentrations of tris(2,4-di-tert-butylphenyl)phosphite, e.g., Irgafos 168, include concentrations that are similar to those of BHT, although lower or higher concentrations may also be employed; suitable concentrations of pentaerythritol tetrakis (3-(3,5-di-tert-butyl-4-hydroxyphenyl) propionate), e.g., Irganox 1010, include similar concentrations although lower or higher concentrations may be employed, e.g., concentrations that are up to about 10%, 20% or 30% higher.

The following examples are set forth to describe the invention in greater detail. They are intended to illustrate, not limit, the invention.

EXAMPLES

Example 1

A master blend, utilizing the formula listed in Table 1, below, was produced. The master blend was divided and spiked with ethinyl estradiol or known anti-oxidants as shown in Table 3. Each blend was then coated on a release liner at a target coat weight of 133 g/m² and dried at 60° C. The sheets were laminated, cut into 15 cm² samples, placed between two release liners, pouched, and then stored at 80° C. Samples were evaluated at five time points as shown in Table 2.

TABLE 1

| Master Blend Formula | |
|---|---|
| Levonorgestrel | 0.38% |
| Penetration Enhancers, PVP/VA, Ethyl Acetate | 39.0% |
| PSA* | 60.5% |

*PSA = polyacrylate adhesive copolymer having a 2-ethylhexyl acrylate monomer and approximately 50-60% w/w of vinyl acetate as a co-monomer

TABLE 2

Sampling Plan

| Sampling Time Point | Temperature | Number of Samples Tested |
|---|---|---|
| 0 days ($T_0$) | 80° C. | 3 |
| 2 days ($T_2$) | 80° C. | 3 |
| 4 days (except Batch 7) ($T_4$) | 80° C. | 3 |
| 6 days (Batch 7 only) ($T_6$) | 80° C. | 3 |
| 8 days ($T_8$) | 80° C. | 3 |

TABLE 3

Test Blends

| Batch #1 | Master Blend |
|---|---|
| Batch #2 | Master Blend + ethinyl estradiol, 1.53 mg/15 cm$^2$ |
| Batch #3 | Master Blend + BHT, 1.14 mg/15 cm$^2$ |
| Batch #4 | Master Blend + BHT, 1.71 mg/15 cm$^2$ |
| Batch #5 | Master Blend + Irganox 1010, 1.11 mg/15 cm$^2$ + Irgafos 168, 0.57 mg/15 cm$^2$ |
| Batch #6 | Master Blend + Irganox 1010, 1.66 mg/15 cm$^2$ + Irgafos 168, 0.85 mg/15 cm$^2$ |
| Batch #7 | Master Blend + ethinyl estradiol, 0.97 mg/15 cm$^2$ |

The amounts of levonorgestrel in each composition at each time point are shown in Table 4 as an average of 3 samples of each batch as a percentage of the target amount of levonorgestrel ("%TL"), which is 0.868% based on the weight of the polymeric matrix.

TABLE 4

Levonorgestrel Stability as % Target Levonorgestrel

| Batch | $T_0$ | $T_2$ | $T_4$ | $T_6$ | $T_8$ |
|---|---|---|---|---|---|
| Batch 1 | 96.9 | 87.1 | 68.5 | NA | 48.1 |
| Batch 2 | 106.6 | 92.8 | 93.3 | NA | 87.3 |
| Batch 3 | 106.8 | 102.0 | 98.1 | NA | 97.7 |
| Batch 4 | 103.4 | 102.2 | 99.7 | NA | 95.7 |
| Batch 5 | 104.3 | 104.3 | 99.4 | NA | 94.6 |
| Batch 6 | 102.6 | 101.1 | 98.5 | NA | 93.1 |
| Batch 7 | 105.4 | 97.1 | NA | 93.4 | 91.7 |

These results demonstrate that ethinyl estradiol functions as an anti-oxidant in the composition and that levonorgestrel stability is markedly improved by addition of an anti-oxidant to the composition.

Example 2

To six batches of a master blend of levonorgestrel, penetration enhancers, polyvinylpyrrolidone/vinyl acetate copolymer, and pressure sensitive adhesive, substantially as described in Example 1, BHT was added at different amounts ranging from 0.02 mgs per patch (each patch contains 300 mgs of master blend) to 1.7 mgs per patch (the value of 1.7 mgs represents the molar equivalent of the amount of levonorgestrel in each patch).

Each batch was heated to 80° C. and analyzed at the time points of 0, 4 and 8 days. All BHT loading values had a positive effect on the stability of levonorgestrel. The amounts of LNG remaining at T=Day 0, T=Day 4, and T=Day 8 are shown in Table 5.

TABLE 5

Effect of BHT concentration on the degradation of levonorgestrel

| BHT (mg/patch) | Day 0 | Day 4 | Day 8 |
|---|---|---|---|
| 0 | 98 | 56 | 56 |
| 1.7 | 100 | 95 | 91 |
| 0.3 | 102 | 98 | 91 |
| 0.15 | 101 | 94 | 85 |
| 0.075 | 98 | 90 | 69 |
| 0.040 | 101 | 74 | 62 |
| 0.020 | 100 | 66 | 66 |

Example 3

The following test batches were prepared and tested as described.

a) Levonorgestrel (2.6 mg) was dissolved in 412 mg Duro Tak 87-4098 (hereinbelow, "Carrier"). Drawdowns were made and heated at 80° C. for 4 and 8 days. The amounts of levonorgestrel remaining and the percent of degradants for the samples heated at 4 and 8 days were determined.

b) Levonorgestrel (2.6 mg) and 60 mg of PVP/VA were dissolved in 412 mg of Carrier. Drawdowns were made and heated at 80° C. for 4 and 8 days. The amounts of levonorgestrel remaining and the percent of degradants for the samples heated at 4 and 8 days were determined.

c) Levonorgestrel (2.6 mg), 1.71 mg BHT and 60 mg PVP/VA were dissolved in 412 mg Carrier. Drawdowns were made and heated at 80° C. for 4 and 8 days. The amounts of levonorgestrel remaining and the percent of degradants for the samples heated at 4 and 8 days were determined.

d) The same procedure as described in c) was performed, except 1.14 mg BHT was added.

The batch formulations are summarized in Table 6.

TABLE 6

Summary of Batch Formulations

|   | Carrier (mg) | levonorgestrel(mg) | PVP/VA(mg) | BHT(mg) |
|---|---|---|---|---|
| a | 412 | 2.6 |  |  |
| b | 412 | 2.6 | 60 |  |
| c | 412 | 2.6 | 60 | 1.71 |
| d | 412 | 2.6 | 60 | 1.14 |

HPLC analysis was conducted to identify degradants of levonorgestrel. An aliquot of approximately 200 mg and 100 mg of the sample (exact weight recorded) for 4 and 8 day stability was used. The sample was dissolved in 5 mL of 1:1 tetrahydrofuran:methanol (THF/MeOH). 10 µL was injected for HPLC analysis.

Levonorgestrel degradants appeared after incubation in the 80° C. oven for 4 days and 8 days for samples a and b. No degradant was found for samples c and d. The results are shown in Table 7.

TABLE 7

Peak Area Percentage of Total Degradants

| Sample ID | Total degradants (%) | |
|---|---|---|
|  | 4 day | 8 day |
| A | 0.48 | 0.75 |
| B | 1.26 | 1.28 |

TABLE 7-continued

Peak Area Percentage of Total Degradants

| Sample ID | Total degradants (%) | |
|---|---|---|
| | 4 day | 8 day |
| C | 0.00 | 0.00 |
| D | 0.00 | 0.00 |

The peak area percentages of remaining levonorgestrel after incubation in 80° C. oven are shown in Table 8.

TABLE 8

Peak Area Percentage of Remaining Substances

| Sample ID | Remaining 4 day | Remaining 8 day |
|---|---|---|
| a | 99.52 | 99.25 |
| b | 98.74 | 98.72 |
| c | 100.00 | 100.00 |
| d | 100.00 | 100.00 |

Note for Table 8:
Remaining levonorgestrel percentages were directly obtained from peak area percentages.

The force degradation study described above indicated that addition of BHT reduced degradation of levonorgestrel, while addition of Povidone (PVP) slightly increased the degradation.

Example 4

Transdermal delivery patches were prepared comprising penetration enhancers, polyvinylpyrrolidone/vinyl acetate copolymer, pressure sensitive adhesive, and varying amounts of levonorgestrel (LNG) and BHT, as follows:
Lot 1: LNG (2.17 mg, 0.87 wt %)–12.5 cm² patch;
Lot 2: LNG (2.6 mg, 0.87 wt %) plus BHT (1.712 mg, 0.57 wt %)–15 cm² patch;
Skin flux across human cadaver skin (3 donor skin samples, 3 replicates per skin donor) was compared. Data are reported in Table 9.

TABLE 9

Cumulative amounts of LNG permeated as a function of time.

| Lot # | Cumulative amounts of LNG permeated (ug/cm²) | | | | | | |
|---|---|---|---|---|---|---|---|
| | 24 h | 48 h | 72 h | 96 h | 120 h | 144 h | 168 h |
| 1 | 5.503 +/− 1.475 | 12.414 +/− 2.456 | 18.787 +/− 3.256 | 24.962 +/− 3.895 | 30.502 +/− 4.569 | 35.767 +/− 5.230 | 40.736 +/− 5.770 |
| 2 | 5.187 +/− 1.900 | 11.336 +/− 2.755 | 17.092 +/− 3.578 | 22.650 +/− 4.286 | 27.795 +/− 4.969 | 32.689 +/− 5.551 | 37.355 +/− 6.110 |

The mean steady-state flux of levonorgestrel (ug/cm²/h) in each batch is shown in the following table.

TABLE 10

Mean steady-state flux of levonorgestrel (ug/cm²/h)

| Lot 1 | 0.2442 +/− 0.0312 |
|---|---|
| Lot 2 | 0.2231 +/− 0.0312 |

These data show that permeation of levonorgestrel was not impeded by the addition of BHT.

Example 5

As shown in Table 11, seven transdermal compositions, each comprising approximately 164.8 mg Duro Tak® 87-4098 and 2.6 mg levonorgestrel (LNG), after drying, with and without PVP/VA and DMSO, were prepared to test the oxidative effects of a polyacrylate PSA, PVP, and DMSO.

TABLE 11

Compositions

| Composition # | PVP/VA (mg) | DMSO (mg) |
|---|---|---|
| 1 | None | none |
| 2 | 60 mg PVP/VA | none |
| 3 | 60 mg PVP/VA | none |
| 4 | 60 mg PVP/VA | none |
| 5 | 60 mg PVP/VA | none |
| 6 | None | 16 mg DMSO |
| 7 | 60 mg PVP/VA | 16 mg DMSO |

In the case of compositions 1-4 and 6, the PSA was pre-heated at 78° C. for 8 hours prior to addition of PVP/VA and DMSO. In the case of preparations 3 and 4, the PVP/VA was pre-heated at 80° C. for 48 hours in the presence of air and nitrogen, respectively.

All preparations were then placed in an oven at 80° C. for 4 days and 8 days. Degradants were analyzed by HPLC. Degradant percentage data are provided in Table 12.

TABLE 12

Peak Area Percentage of Total Degradants

| Composition # | Degradants (%) Day 4 | Degradants (%) Day 8 |
|---|---|---|
| 1 | 0.32 | 0.47 |
| 2 | 0.76 | 0.94 |
| 3 | 0.87 | 0.91 |
| 4 | 0.78 | 1.16 |
| 5 | 1.21 | 1.60 |
| 6 | 1.12 | 1.67 |
| 7 | 1.65 | 1.78 |

As shown in Table 12, presence of PVP/VA increased degradants roughly by two-fold. Pre-treatment of PVP/VA did not show significant difference. Heating the compositions for 8 days produced slightly more degradants than for 4 days. Pre-heating the PSA reduced the amount of degradants. Addition of DMSO increased the amount of degradants.

Example 6

A master blend utilizing the formula listed in Table 13 was produced. The master blend was then divided and spiked with BHT as shown in Table 14. Each test blend was then coated on a release liner at a target coat weight of 200 g/m² and dried at 60° C. for 17.5 mins using a fan speed of 2300 rpm. The sheets were then laminated, cut into 15 cm² samples, placed between two release liners, pouched, and then stored at 80° C. Samples were evaluated on Days 0, 4, and 8.

TABLE 13

Master Blend Formula

| | |
|---|---|
| Levonorgestrel | 0.378% |
| Ethinyl estradiol | 0.333% |
| Penetration Enhancers, PVP/VA, Ethyl Acetate | 39.558% |
| PSA* | 59.730% |

*PSA = polyacrylate adhesive copolymer having a 2-ethylhexyl acrylate monomer and approximately 50-60% w/w of vinyl acetate as a co-monomer [Duro-Tak 87-4098]

TABLE 14

Test Blends

| | |
|---|---|
| Batch #1 | Master Blend |
| Batch #2 | Master Blend + BHT, 1.712 mg/15 cm², 2.481 g/kg |
| Batch #3 | Master Blend + BHT, 1.000 mg/15 cm², 1.449 g/kg |
| Batch #4 | Master Blend + BHT, 0.428 mg/15 cm², 0.620 g/kg |
| Batch #5 | Master Blend + BHT, 0.300 mg/15 cm², 0.435 g/kg |
| Batch #6 | Master Blend + BHT, 0.150 mg/15 cm², 0.217 g/kg |

The amounts of levonorgestrel and ethinyl estradiol were determined by HPLC. The results (% LC) for each test blend are shown in Table 15 as an average of 5 samples per test blend, with %-Relative Standard Deviations (%RSD).

TABLE 15

Results

| Test Blend | Day 0 EE (% RSD) | Day 0 LNG (% RSD) | Day 4 EE (% RSD) | Day 4 LNG (% RSD) | Day 8 EE (% RSD) | Day 8 LNG (% RSD) |
|---|---|---|---|---|---|---|
| Control | 98.7 (1.9) | 100.3 (2.1) | 77.3 (1.0) | 43.0 (3.1) | 72.9 (9.1) | 28.5 (57.0) |
| 2 | 98.0 (2.2) | 98.7 (2.2) | 91.4 (1.3) | 72.1 (1.5) | 85.4 (2.4) | 57.5 (8.1) |
| 3 | 99.1 (1.8) | 99.6 (2.0) | 87.8 (2.6) | 66.7 (2.1) | 86.9 (2.6) | 54.4 (22.8) |
| 4 | 99.3 (3.1) | 100.2 (3.0) | 85.7 (3.0) | 51.6 (9.4) | 79.8 (5.9) | 33.9 (48.6) |
| 5 | 97.4 (1.8) | 98.2 (1.9) | 81.0 (1.8) | 54.7 (6.4) | 82.6 (3.3) | 41.8 (33.6) |
| 6 | 98.5 (1.2) | 99.6 (1.1) | 80.4 (6.1) | 38.9 (51.5) | 81.0 (1.6) | 41.5 (7.1) |

It is understood that the examples and embodiments described herein are for illustrative purposes only and that various modifications or changes in light thereof will be suggested to persons skilled in the art and are to be included within the spirit and purview of this application and the scope of the appended claims.

The invention claimed is:

1. An adhesive polymer matrix composition for transdermal delivery of levonorgestrel, wherein the matrix comprises:
    a) a polymeric pressure sensitive adhesive (PSA)
    b) levonorgestrel,
    c) a skin permeation enhancer comprising an organic solvent,
    d) polyvinyl pyrrolidone (PVP) or a PVP copolymer, and
    e) an anti-oxidant
    wherein
        (i) the anti-oxidant protects against oxidative degradation of the levonorgestrel by the organic solvent or the PVP or PVP copolymer;
        (ii) the composition lacks and estrogen; and
        (iii) the stability of the composition is improved over the stability of such composition lacking and anti-oxidant.

2. The composition of claim 1, wherein the PSA is a polyacrylate adhesive, a polyisobutylene adhesive, or a silicone adhesive and the organic solvent is DMSO.

3. The composition of claim 2, wherein the anti-oxidant is sodium bisulfite, sodium sulfite, isopropyl gallate, Vitamin C, Vitamin E, butylated hydroxyanisole (BHA), butylated hydroxytoluene (BHT), pentaerythritol tetrakis (3-(3,5-di-tert-butyl-4-hydroxiphenyl) propionate), or tris (2,4di-tert-butylphenyl) phosphate or any combination of two or more of said anti-oxidants.

4. The composition of claim 1, wherein the composition further comprises one or more or of: alcohols; alkanones; amides and other nitrogenous compounds; 1-substituted azacycloheptan-2-ones; bile salts; cholesterol; cyclodextrins and substituted cyclodextrins; ethers; saturated and unsaturated fatty acids; saturated and unsaturated fatty acid esters; saturated and unsaturated fatty alcohol esters; glycerides and monoglycerides; organic acids; methyl nicotinate; pentadecalactone; polyols and esters thereof; phospholipids; sulfoxides; surfactants; terpenes; and combinations thereof, as skin permeation enhancers.

5. The composition of claim 1, wherein the organic solvent is dimethyl sulfoxide (DMSO) and wherein the composition further comprises one or more of: a fatty ($C_8$-$C_{20}$) alcohol ester of a hydroxy acid, a lower ($C_1$-$C_4$) alkyl ester of a hydroxy acid, and a $C_6$-$C_{18}$ fatty acid, as the skin permeation enhancers.

6. The composition of claim 4, wherein the organic solvent is DMSO.

7. A method of improving the stability of a progestin transdermal delivery composition comprising
    a) a polymeric pressure sensitive adhesive (PSA)
    b) levonorgestrel,
    c) a skin permeation enhancer comprising an organic solvent, and
    d) polyvinyl pyrrolidone (PVP) or a PVP copolymer;
    wherein the composition lacks an estrogen;
        the method comprising adding an anti-oxidant to the composition, thereby improving the stability of the composition over the stability of such composition lacking the anti-oxidant.

8. The method of claim 7, wherein the PSA is a polyacrylate adhesive, a polyisobutylene adhesive, or a silicone adhesive.

9. The method of claim 7, wherein the anti-oxidant is sodium bisulfite, sodium sulfite, isopropyl gallate, Vitamin C, Vitamin E, butylated hydroxyanisole (BHA), butylated hydroxytoluene (BHT), pentaerythritol tetrakis (3-(3,5-di-tert-butyl-4-hydroxyphenyl)propionate), or tris(2,4-di-tert-butylphenyl) phosphite or any combination of two or more of said anti-oxidants.

10. The method of claim 7, wherein the composition further comprises one or more of: alcohols; alkanones; amides and other nitrogenous compounds; 1-substituted azacycloheptan-2-ones; bile salts; cholesterol; cyclodextrins and substituted cyclodextrins; ethers; saturated and unsaturated fatty acids; saturated and unsaturated fatty acid esters; saturated and unsaturated fatty alcohol esters; glycerides and monoglycerides; organic acids; organic solvents; methyl nicotinate; pentadecalactone; polyols and esters thereof; phospholipids; sulfoxides; surfactants; terpenes; and combinations thereof, as skin permeation enhancers.

11. The method of claim 10, wherein the skin permeation enhancer comprises one or more of: DMSO, a fatty ($C_8$-$C_{20}$) alcohol ester of a hydroxy acid, a lower ($C_1$-$C_4$) alkyl ester of a hydroxy acid, and a $C_6$-$C_{18}$ fatty acid.

12. The composition of claim 1 wherein the organic solvent is DMSO and wherein the stability of the composition is improved over the stability of such composition with ethinyl estradiol but lacking an anti-oxidant.

13. A contraceptive progestin-only composition for transdermal delivery of levonorgestrel that comprises:
   a) a polyacrylate pressure sensitive adhesive (PSA),
   b) levonorgestrel,
   c) a skin permeation enhancer comprising DMSO,
   d) PVP/VA copolymer, and
   e) an anti-oxidant wherein
   (i) the anti-oxidant protects against oxidative degradation of the levonorgestrel by the polyacrylate PSA, the DMSO, or the PVP/VA copolymer,
   (ii) the composition lacks an estrogen,
   (iii) the stability of the levonorgestrel is improved over the stability of levonorgestrel in such composition lacking an anti-oxidant, and
   (iv) the stability of the levonorgestrel is improved over the stability of levonorgestrel in such composition comprising ethinyl estradiol and lacking an anti-oxidant.

14. A contraceptive progestin-only composition for transdermal delivery of levonorgestrel, wherein the composition lacks estrogen and consists of:
   a) a pressure sensitive adhesive,
   b) levonorgestrel,
   c) one or more skin permeation enhancers, at least one of which is an organic solvent,
   d) PVP or a PVP copolymer, and
   e) an anti-oxidant.

* * * * *